United States Patent [19]

Chang et al.

[11] Patent Number: 5,245,860
[45] Date of Patent: Sep. 21, 1993

[54] SENSOR FOR DETECTION OF OIL LEAKS AND OIL QUALITY IN STUFFING BOX OF WALKING BEAM PUMP SYSTEM

[75] Inventors: Victor Chang, S. Antonio de los Altos; Noel Moreno, Carrizales; Cesar Alvarez, Caracas; Gianbattista Urbani, Valencia, all of Venezuela

[73] Assignee: Intevep, S.A., Caracas, Venezuela

[21] Appl. No.: 756,453

[22] Filed: Sep. 9, 1991

[51] Int. Cl.$^5$ .......................... E21B 33/03; G01M 3/04
[52] U.S. Cl. ........................................... 73/40; 166/84; 277/2
[58] Field of Search ................ 73/40, 40.5 R, 46, 151, 73/153, 155, 49.8; 277/2; 166/84

[56] References Cited

U.S. PATENT DOCUMENTS

| | | | |
|---|---|---|---|
| 3,221,593 | 12/1965 | Ferris | 277/2 |
| 3,276,246 | 10/1966 | Truman et al. | 73/40.5 R |
| 3,946,625 | 3/1976 | Miyazaki et al. | 73/54.04 |
| 3,955,822 | 5/1976 | Irby | 277/2 |
| 3,967,678 | 7/1976 | Blackwell | 166/84 |
| 4,135,859 | 1/1979 | Carson et al. | 277/2 |
| 4,295,653 | 10/1981 | Coles | 277/2 |
| 4,901,751 | 2/1990 | Story et al. | 73/40.5 R |
| 4,917,190 | 4/1990 | Coppedge | 277/2 |
| 5,148,699 | 9/1991 | Morse | 73/40 |

FOREIGN PATENT DOCUMENTS 1514977  6/1978  United Kingdom ............... 73/61.48

*Primary Examiner*—Tom Noland
*Assistant Examiner*—George M. Dombroske
*Attorney, Agent, or Firm*—Bachman & LaPointe

[57] ABSTRACT

A method and apparatus for sensing unacceptable oil leaks from a stuffing box in a walking beam pumping system includes a container for receiving leakage from the stuffing box which is divided by a weir into a first compartment and a second compartment wherein the first compartment is provided with an adjustable outlet for setting the acceptable level of stuffing box leakage such that when the acceptable level is exceeded leakage into the second compartment occurs and is sensed by an appropriate sensor (28).

8 Claims, 2 Drawing Sheets

SENSOR FOR DETECTION OF OIL LEAKS AND OIL QUALITY IN STUFFING BOX OF WALKING BEAM PUMP SYSTEM

BACKGROUND OF THE INVENTION

In oil well pumping devices such as the balance beam type it is critical to maintain the integrity of the stuffing box and its packing about the reciprocating pump rod.

Many of these pumping devices are operated unattended in the field and failure of the stuffing box packing can cause loss of large volumes of oil and thus, large economic losses as well as environmental pollution.

Therefore, it is important to provide sensors at the well head for recognizing stuffing box failure and for generating a signal to alert responsible operators to take appropriate action.

A typical prior art device which signals a breakdown of the stuffing box is shown and described in U.S. Pat. No. 3,180,134. In the '134 patent stuffing box is surrounded by a reservoir of oil, produced by the well, maintained at a static fluid pressure which is substantially higher than the pressure at which the oil is produced from the well. A drop in oil pressure in the reservoir is a strong indication that the stuffing box is leaking. The differential in oil pressure is read and an appropriate sensor responds to the pressure drop and creates a signal notifying interested operators of the leaky stuffing box.

Another prior art sensing device is disclosed and described in U.S. Pat. No. 3,276,246 in which oil from a leaking main stuffing box is retained by an auxiliary stuffing box and thereafter directed to a reservoir. When the level of fluid in the reservoir reaches a certain level an appropriate alarm is sounded.

SUMMARY OF THE INVENTION

Therefore, it is a primary feature of the present invention to provide a novel method for detecting excessive, unacceptable product leakage in the stuffing box of a walking beam pumping system.

A further feature of the invention is the provision of a sensor that distinguishes between usual and customary leakage and excessive, unacceptable leakage.

A further feature of the invention is the provision of a sensor which detects variations in fluid opacity.

A still further feature of the invention is the provision of a photoelectric means for sensing opacity of a fluid and utilizing the degree of opacity as a measure of oil well product quality.

A still further feature of the invention is the provision of a container having an overflow weir for dividing the container in two compartments wherein one compartment receives normal stuffing box leakage and a second compartment receives stuffing box leakage that overflows the weir thereby signalling excessive, abnormal and unacceptable leakage.

A further feature of the invention is the provision of a variable, adjustable orifice in said first compartment which cooperates with the volume of the first compartment and with the height of the weir to set an acceptable level of stuffing box leakage.

A method enhancing certain principles of the present invention may comprise providing a container for receiving stuffing box leakage, dividing the container into two compartments by means of an overflow weir, directing stuffing box leakage to a first compartment for containing an acceptable level of stuffing box leakage whereby when said stuffing box leakage becomes excessive, fluid in said first compartment overflows said weir into a second compartment and utilizing a sensing means in said second compartment to detect the presence of fluid in said second compartment to generate a pump shut down signal.

An apparatus embracing certain other principles of the invention may comprise a container for receiving stuffing box oil leakage, a weir means dividing said container into a first compartment and a second compartment, said first compartment being operable to receive stuffing box leakage at an acceptable level and said second compartment being empty normally, a sensing means connected to said second compartment for detecting the presence of fluid in said second compartment when fluid from said first compartment overflows said weir means thereby signalling excessive and unacceptable stuffing box leakage.

Other features and advantages of the invention will become more apparent from an examination of the succeeding specification when read in conjunction with the appended drawings, in which;

DETAILED DESCRIPTION OF THE INVENTION

Figure 1:
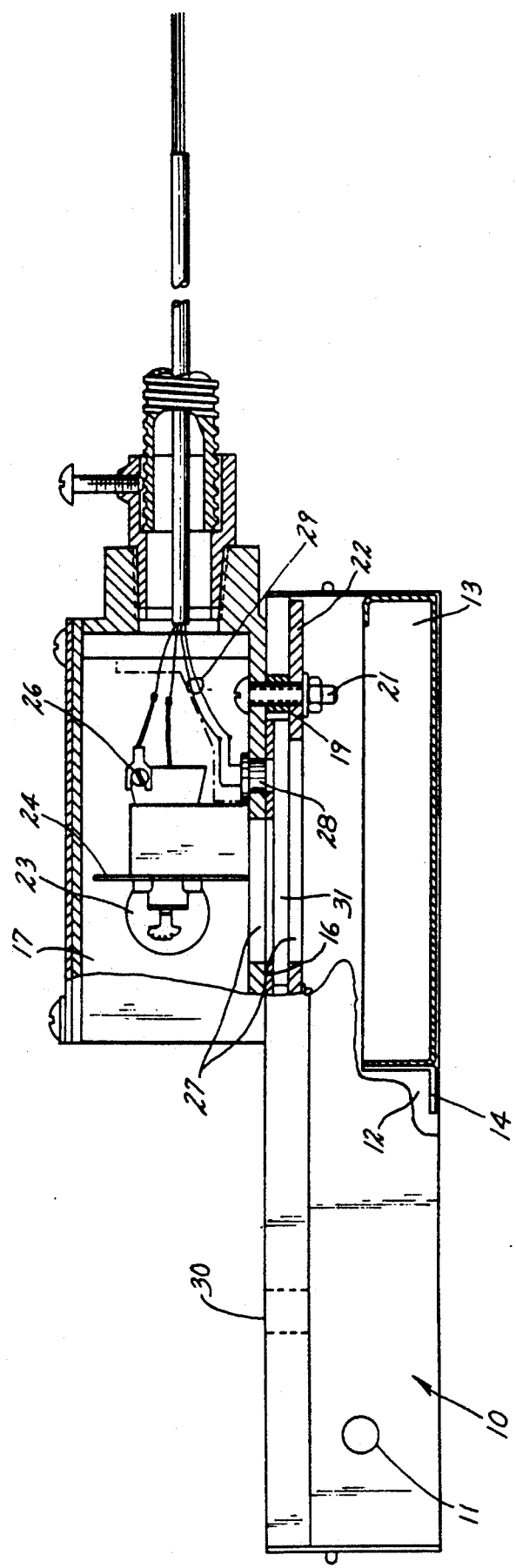
FIG. 1 is a partial vertical section of a sensor unit of the present invention.

As shown in FIG. 1, a fluid container 10 having an adjustable discharge orifice 11 is divided into a first compartment 12 and a second compartment 13 by a weir 14.

The compartment 12 includes an inlet 30 through which leakage from the stuffing box of a walking beam pump is directed.

When stuffing box leakage is normal, the compartment 12 is adequate to contain normal leakage.

To provide for long periods of unattended operation of the pump and to minimize frequency of inspection of the pump in the field, the discharge orifice 11 is adjusted, relative to the volume of the compartment and the height of the weir 14, to an opening that corresponds to an acceptable fluid level or normal flow of stuffing box leakage.

That is, it is well-known that a certain amount of stuffing box leakage is normal and desirable to provide adequate lubrication of the pump rod and to prevent seizing.

When stuffing box leakage exceeds acceptable levels the fluid (oil or oil and water mixture) flowing into compartment 12 exceeds the outflow through orifice 11. When this occurs, fluid overflows weir 14 into normally empty compartment 13.

Sealed to the compartment 13 via a neoprene gasket 16 is a third compartment 17 which houses a sensing means 28 in the form of a photoelectric cell or the like. A protective window 31 is provided between gasket 16 and compartment 13.

The gasket 16 and protective window 31 precludes the entry of oil, water or a mixture of oil and water into the compartment 17.

Springs 19 (only one shown) and bolt and nut assembly 21 secures the compartment 17 to a lid 22 of the container 10 over compartment 13.

A light source 23 (incandescent lamp) is supported in socket 24 within compartment 17 and is energized by leads 26 and illuminates compartment 13 through observation window 27.

The photoelectric cell 28 reads the intensity of light reflected from the compartment 13 in well-known fashion to be described hereinbelow.

The cell 28 transmits an electrical signal via leads 29 which is a measure of the intensity of light reflected from light source 23.

As will become more apparent hereinafter, the compartment 13, which under ideal leakage conditions would be normally empty, in abnormal leakage conditions receives fluid overflowing weir 14 where the fluid (oil, water or a mixture of oil and water) represents a wide range of opacity and thus a wide range of reflected light. That is, the reflected light varies from that reflected by an empty compartment 13 to the reflection developed by the opacity of the particular fluid overflowing the weir and contained in compartment 13.

Thus the signal generated by the photoelectric cell in "reading" the intensity of the reflected light serves not only to sense the presence of overflow fluid but also serves to provide a measure of the quality of the oil pumped by the walking beams.

That is, raw crude having a minimum of water or other extraneous material develops a reflective index which is identifiable from a reflective index generated by crude which is contaminated by water, mud, etc.

Therefore, when an excessive amount of leakage occurs in the pump stuffing box, fluid overflows the weir 14 and this occurrence is "read" by the photoelectric cell 28 and the electrical signal generated is directed to an operator alerting him to take action such as shut down the pump.

In addition, the signal from the photoelectric cell may be compared to a quality calibration which indicates the quality of the product being pumped.

Figure 2:
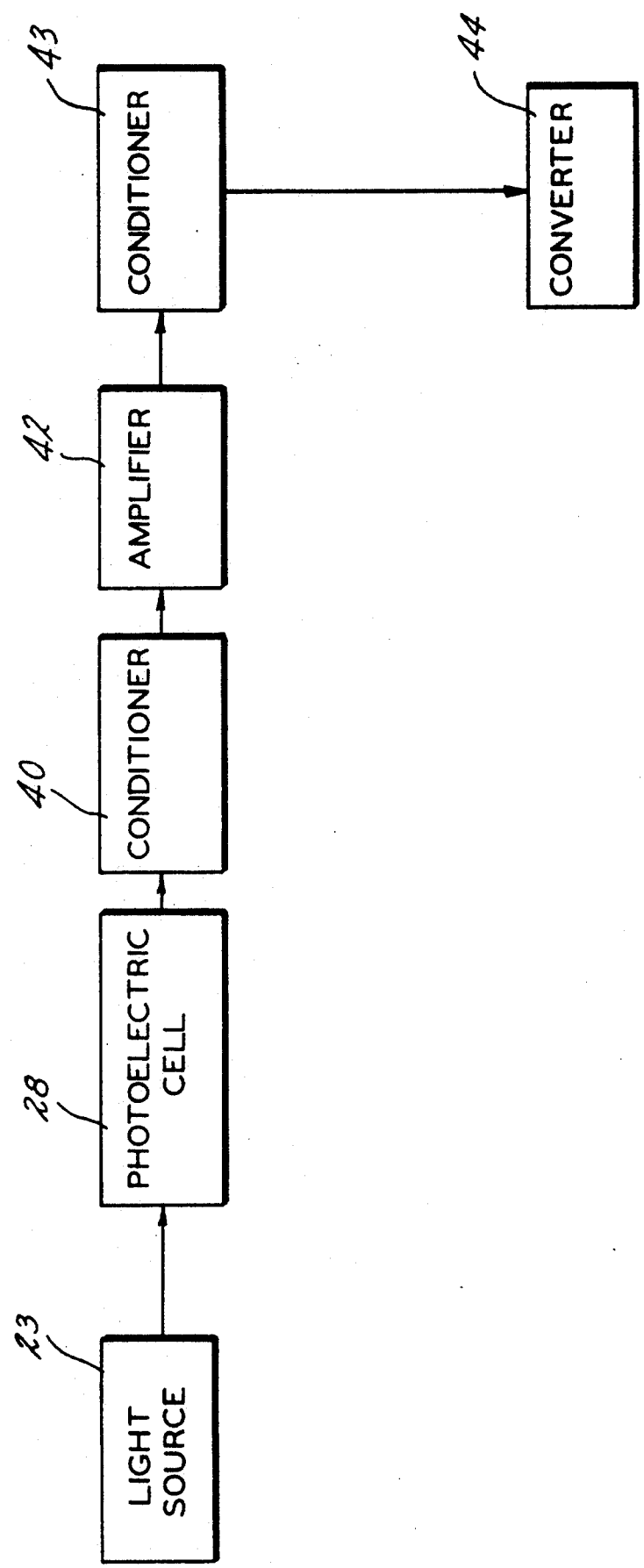
FIG. 2 is a block diagram of the electrical circuitry associated with the invention.

FIG. 2 is a flow diagram of a typical electrical circuit useful with the sensing device of the present invention. The reflected light from light source 23 is sensed by photoelectric cell 28 which sends a signal to conditioner 40. Conditioner 40 converts the signal from cell 28 into voltage which is then fed to amplifier 42. The conditioner 40 is formed, for example, by a resistance bridge as is well-known in the art. Conditioner 44 receives the amplified voltage from amplifier 42 which is normalized to the range of 0-10 VDC. Converter 44 converts the voltage signal to a current signal. The signal displayed a cathode ray tube or other appropriate displays means to present a visual representation of leakage level and to make a comparison of the signal to a calibrated standard for indicating the quality of the product.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

We claim:

1. In a walking beam oil well pumping system having the usual and customary reciprocating pump rod and stuffing box assembly, a method of distinguishing between acceptable stuffing box oil leakage and unacceptable oil leakage comprising:
   providing a container for receiving stuffing box leakage;
   dividing the container into a first compartment and a second compartment by means of an overflow weir;
   providing an adjustable outlet means in said first compartment;
   directing stuffing box leakage to a first compartment for containing an acceptable level of stuffing box leakage whereby when said stuffing box leakage becomes excessive fluid in said first compartment overflows said weir into a second compartment;
   adjusting said outlet means to a predetermined size corresponding to an acceptable level of stuffing box leakage whereby no fluid overflows said weir when said leakage is acceptable; and
   sensing the presence of fluid in said second compartment to generate a pump shut down signal.

2. The method of claim 1 wherein the sensing means is a photoelectric means.

3. The method of claim 1 in which the sensing means is sensitive to changes in opacity of fluid collected in said second compartment.

4. The method of claim 1 in which the photoelectric means is operable to detect and signal changes in liquid opacity and utilizing the signals as a measure of oil product quality.

5. An apparatus for detecting excessive leakage in the stuffing box of a walking beam oil pumping system comprising:
   a container for receiving stuffing box oil leakage;
   a weir means dividing said container into a first compartment and a second compartment, said first compartment having an adjustable outlet means for setting the acceptable level of stuffing box leakage wherein said first compartment receives stuffing box leakage and said second compartment is normally free of leakage; and
   a sensing means for detecting the presence of fluid in said second compartment when fluid from said first compartment overflows said weir means thereby signalling excessive and unacceptable stuffing box leakage.

6. The apparatus of claim 5 wherein the sensing means is a photoelectric cell.

7. The apparatus of claim 6 in which the photoelectric cell is enclosed in a third compartment which overlays the second compartment, and
   seal means is disposed between the second and third compartments to prevent entry of fluid into the third compartment.

8. The apparatus of claim 7 in which the photoelectric cell is shielded by a sheet of transparent material for protecting the photoelectric cell and to provide an observation window into said second compartment.

* * * * *